(12) United States Patent
Yatagai et al.

(10) Patent No.: US 7,710,577 B2
(45) Date of Patent: May 4, 2010

(54) MULTIPLEXING SPECTRUM INTERFERENCE OPTICAL COHERENCE TOMOGRAPHY

(75) Inventors: Toyohiko Yatagai, Nagareyama (JP); Yoshiaki Yasuno, Tsukuba (JP)

(73) Assignee: University of Tsukuba, Ibaraki (JP)

( * ) Notice: Subject to any disclaimer, the term of this patent is extended or adjusted under 35 U.S.C. 154(b) by 555 days.

(21) Appl. No.: 11/572,803

(22) PCT Filed: Mar. 17, 2005

(86) PCT No.: PCT/JP2005/004800

§ 371 (c)(1),
(2), (4) Date: Feb. 6, 2007

(87) PCT Pub. No.: WO2006/016434

PCT Pub. Date: Feb. 16, 2006

(65) Prior Publication Data
US 2008/0002183 A1    Jan. 3, 2008

(30) Foreign Application Priority Data
Aug. 9, 2004    (JP) ............................... 2004-232768

(51) Int. Cl.
G01B 9/02    (2006.01)
G01B 11/02   (2006.01)
(52) U.S. Cl. ...................................... 356/492; 356/497
(58) Field of Classification Search ................ 356/479, 356/497, 492
See application file for complete search history.

(56) References Cited

U.S. PATENT DOCUMENTS 6,377,349 B1 *    4/2002    Fercher ..................... 356/497

(Continued)

FOREIGN PATENT DOCUMENTS

JP    10-325795 A    12/1998

(Continued)

OTHER PUBLICATIONS

Yoshiaki Anno, Journal of the Japan Society of Precision Engineering, vol. 70, No. 5, May 5, 2004, pp. 614-617.

(Continued)

Primary Examiner—Gregory J Toatley, Jr.
Assistant Examiner—Scott M Richey
(74) Attorney, Agent, or Firm—Law Office of Katsuhiro Arai

(57) ABSTRACT

The present invention achieves multiplexing spectrum interference optical coherence tomography capable of full-range OCT measurement that causes no delays in measurement time due to high-order scans and is also free from complex conjugated images. This multiplexing spectrum interference optical coherence tomography comprises: a first beam splitter 3 positioned in an optical path 2 from a light source 1 and used to separate an object light 4 and a reference light 5; a galvano mirror 6 positioned in the optical path of the object light 4 and used to scan the object light onto a measured object 8; a second beam splitter 10 positioned in the optical path of the reference light 5; a first reference mirror 12 positioned in the optical path of a first reference light 11 separated by the second beam splitter 10; a second reference mirror 15 positioned in the optical path of a second reference light 13 separated by the second beam splitter 10; and a chopper 16 that passes the first reference light 11 and second reference light 13 alternately.

4 Claims, 8 Drawing Sheets

U.S. PATENT DOCUMENTS

| | | |
|---|---|---|
| 7,075,658 B2 * | 7/2006 | Izatt et al. .................... 356/479 |
| 7,355,716 B2 * | 4/2008 | de Boer et al. .............. 356/479 |
| 7,548,320 B2 * | 6/2009 | Chan et al. .................. 356/497 |

FOREIGN PATENT DOCUMENTS

| | | |
|---|---|---|
| JP | 11-325849 | 11/1999 |
| JP | 2000-002506 | 1/2000 |
| JP | 2002-82045 A | 3/2002 |
| JP | 2002-310897 | 10/2002 |
| JP | 2004100741 * | 3/2004 |
| JP | 2005-083929 | 3/2005 |
| WO | WO 98/53733 | 12/1998 |

OTHER PUBLICATIONS

Yoshiaki Anno, O plus E. No. 288, Jan. 1, 2003, pp. 1254-1259.

* cited by examiner

[Fig. 1]
(a)
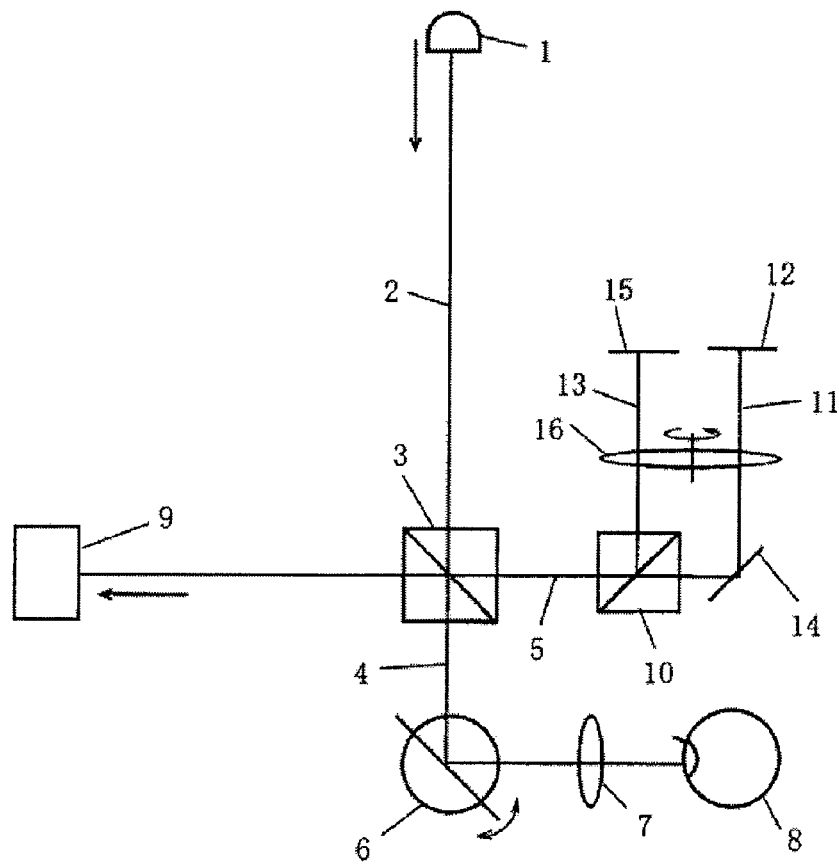
(b)
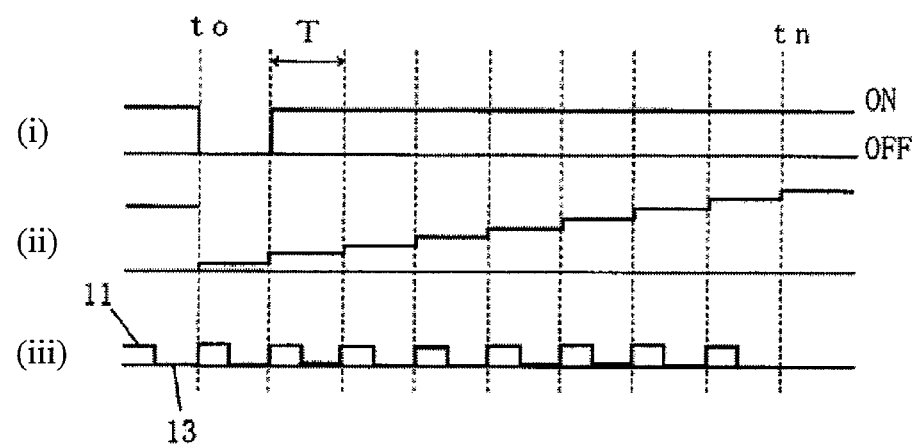

[Fig. 2]
(a)
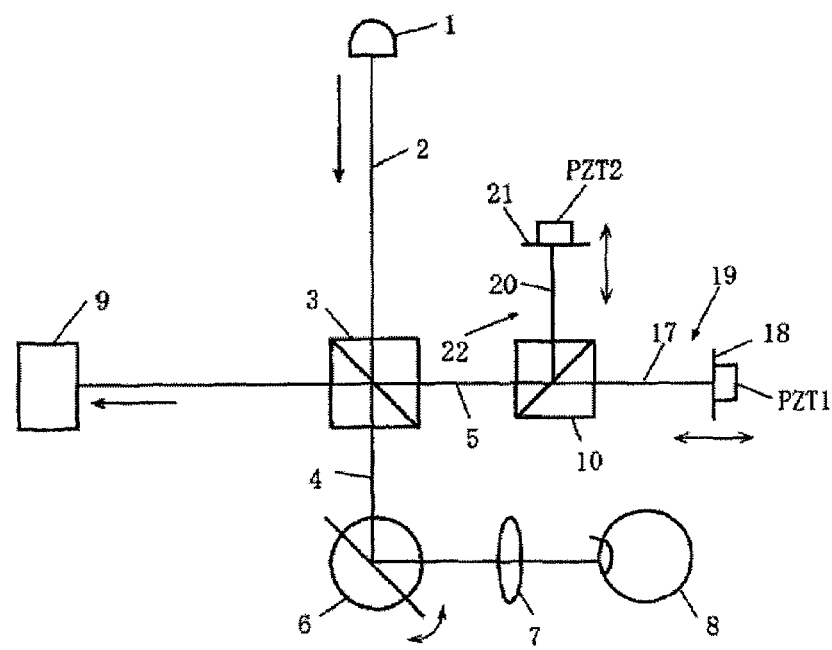
(b)
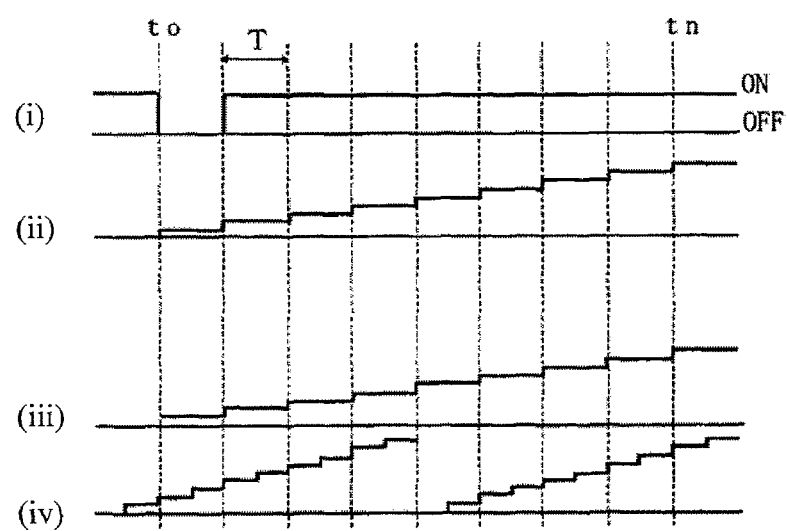

[Fig. 3]
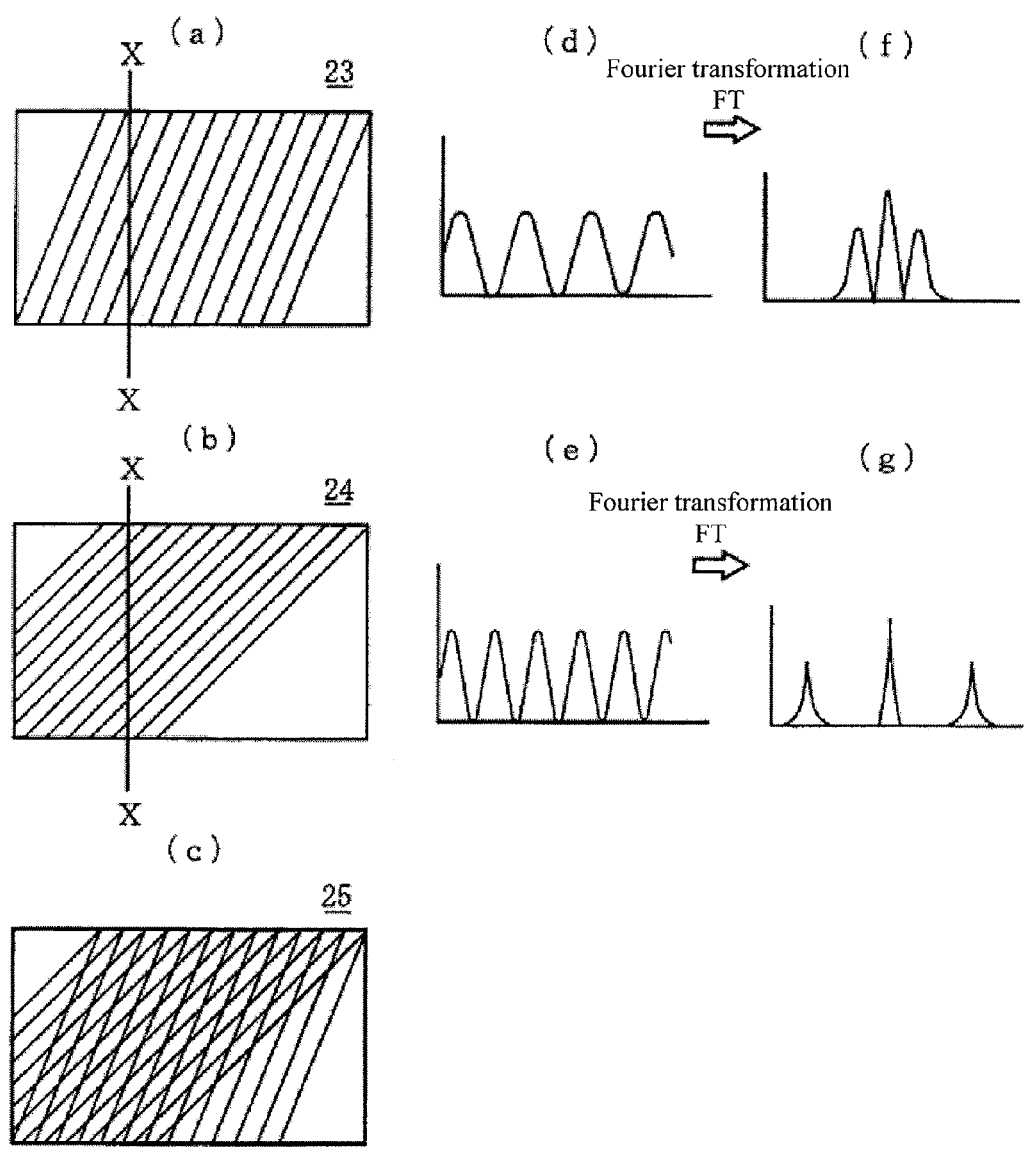

[Fig. 4]
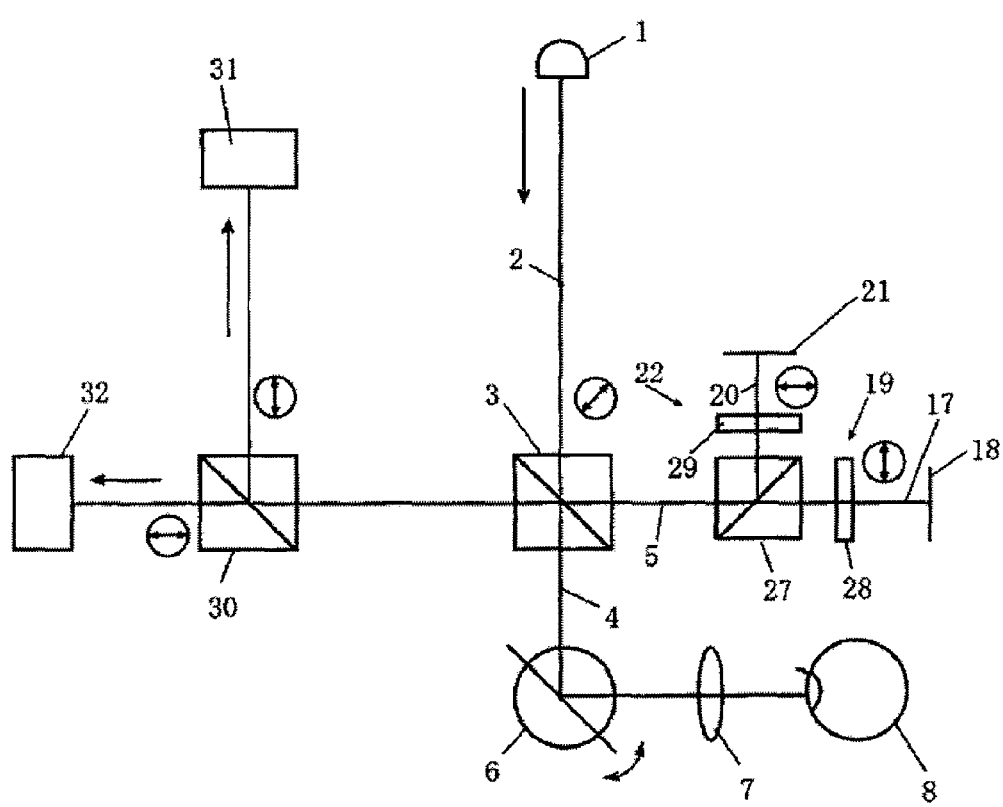

[Fig. 5]
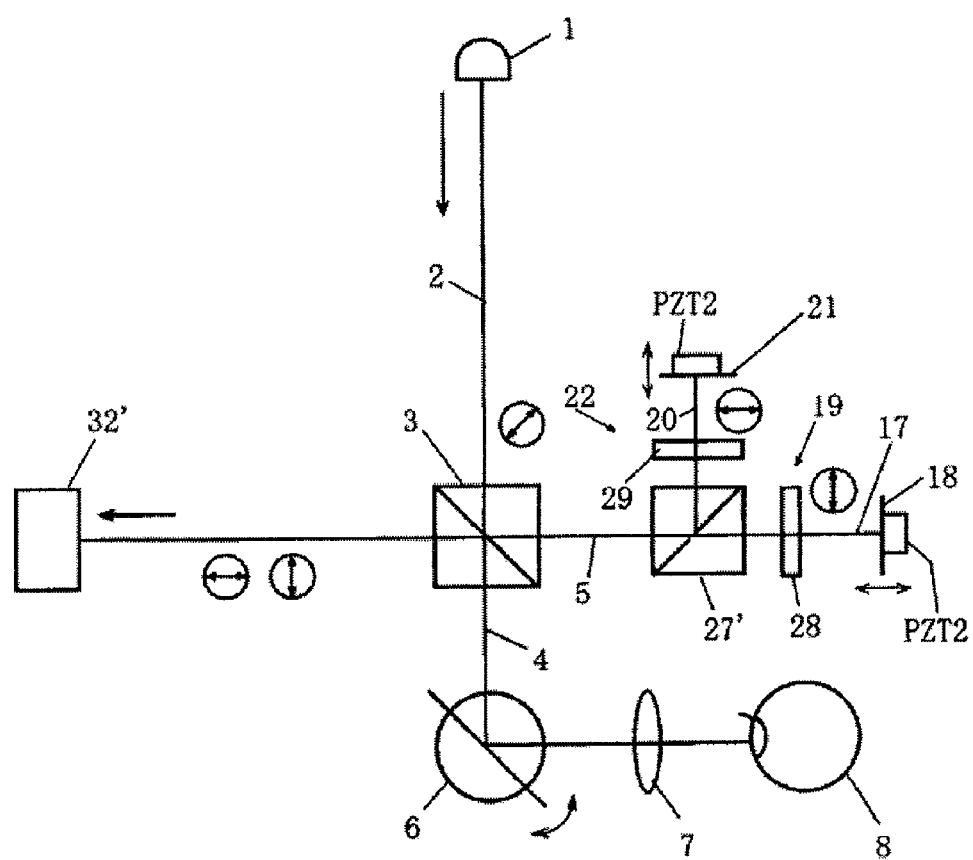

[Fig. 6]
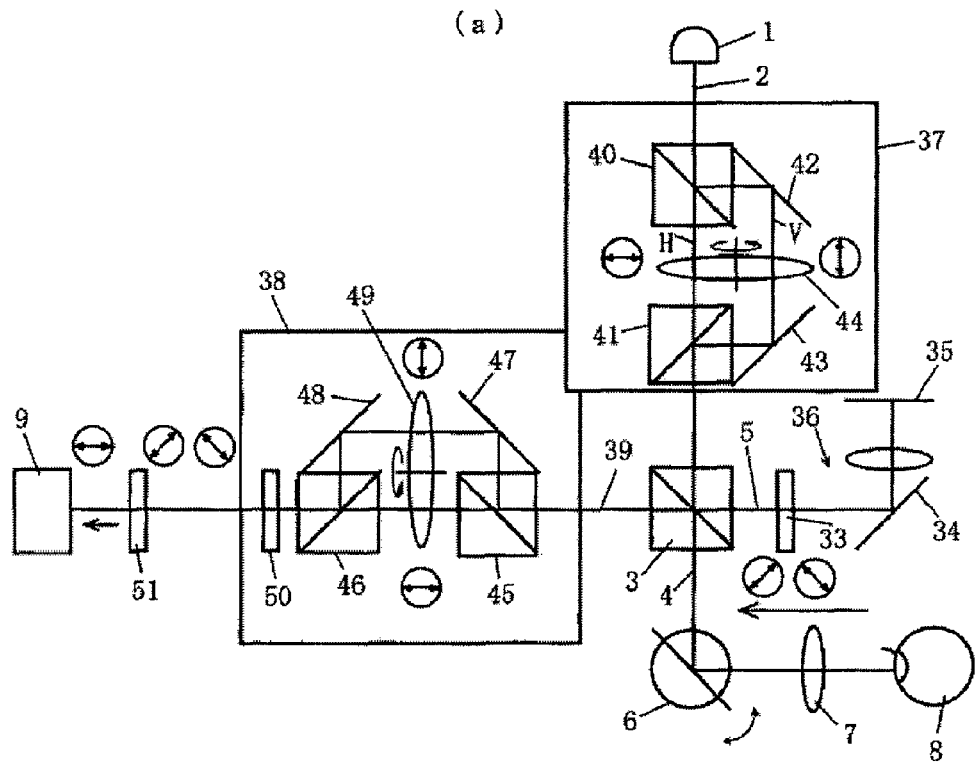
(a)
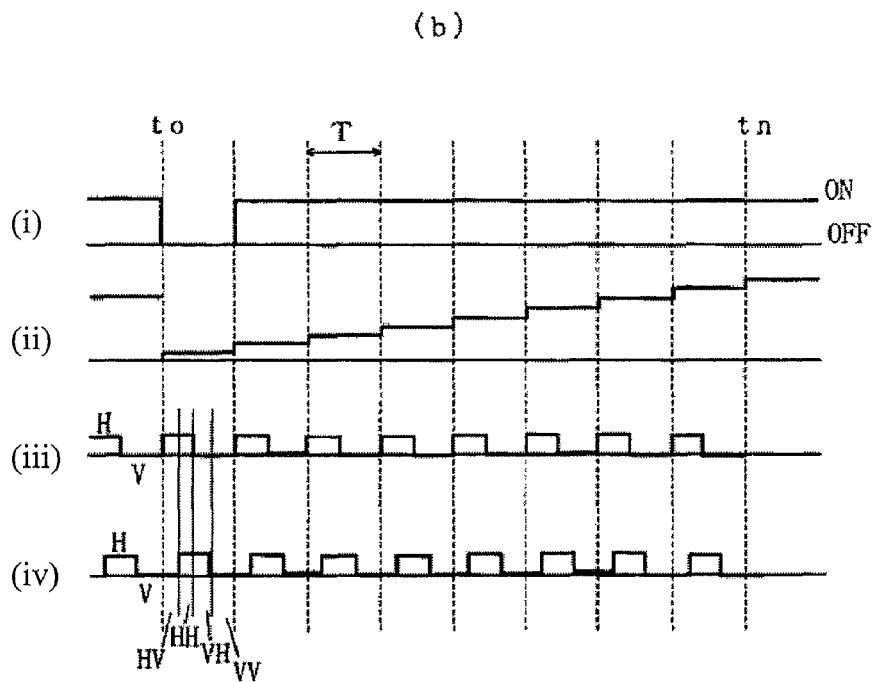
(b)

[Fig. 7]
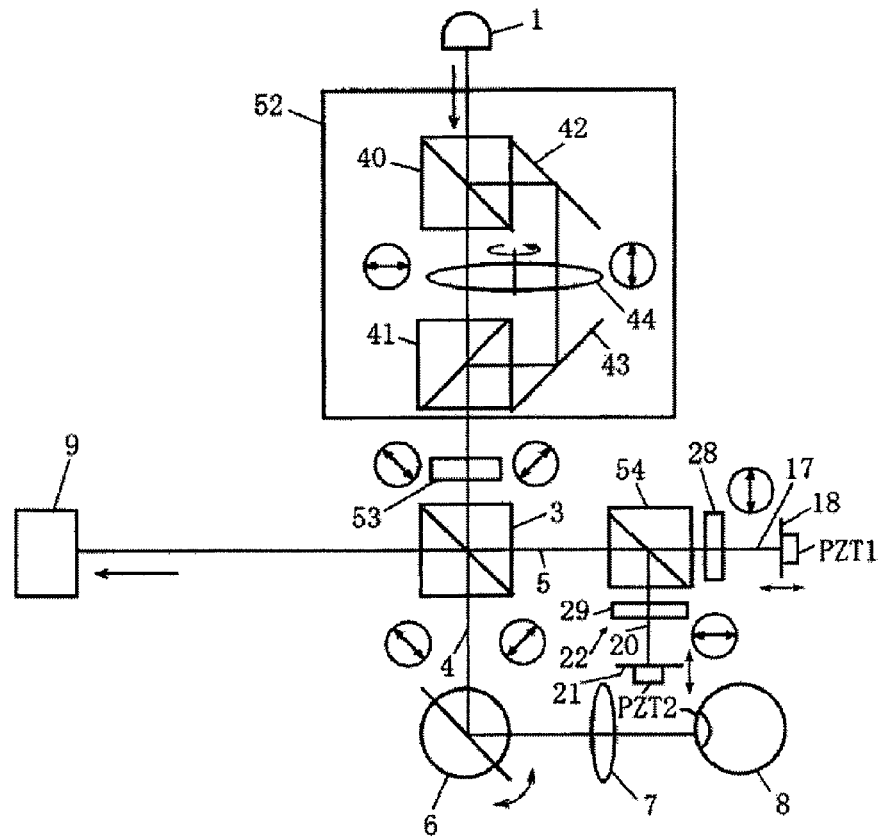
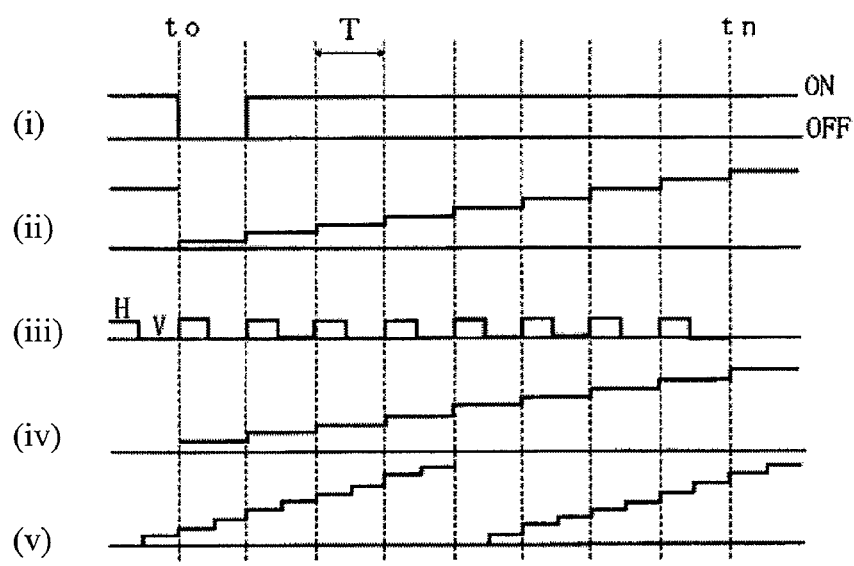

[Fig. 8]
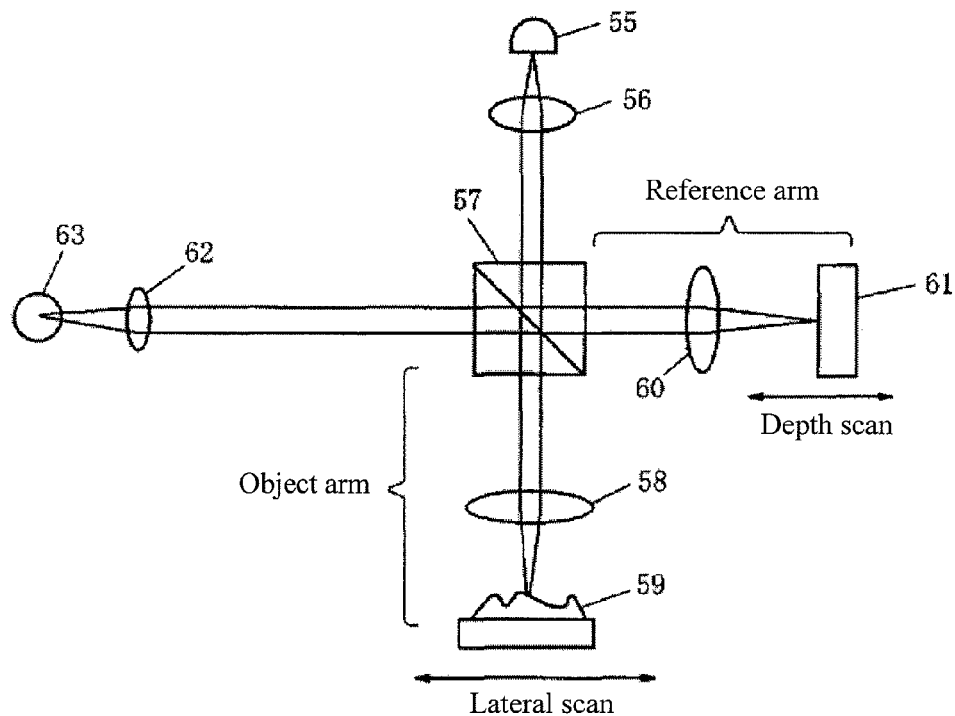
[Fig. 9]
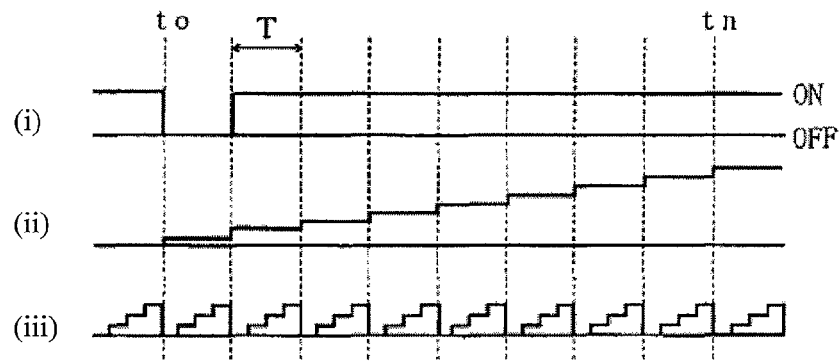

MULTIPLEXING SPECTRUM INTERFERENCE OPTICAL COHERENCE TOMOGRAPHY

This application is the U.S. National Phase under 35 U.S.C. §371 of International Application PCT/JP2005/004800, filed Mar. 17, 2005, which claims priority to Japanese Patent Application No. 2004-232768, filed Aug. 9, 2004. The International Application was published under PCT Article 21(2) in a language other than English.

TECHNICAL FIELD OF THE INVENTION

The present invention relates to multiplexing spectrum interference optical coherence tomography that also uses other techniques such as time division and polarization division.

BACKGROUND ART

The tomographic measurement method that uses light having low temporal coherence as a probe, called "Optical Coherence Tomography" (OCT), is one type of nondestructive tomographic measurement technology used in medical and other fields (refer to Patent Literature 1). OCT uses light as a measurement probe, and therefore provides the advantage of being able to measure refractive index distribution, spectrum information and polarization information (double refractive index distribution), among others, regarding the measured sample.

General OCT is based on Michelson's interferometer, and its operating principles are explained in FIG. 8. Light emitted from the light source 63 is split into parallel beams through the collimator lens 62 and then divided into reference light and object light by the beam splitter 57. The object light is focused onto the measured sample 59 through the object lens 58 in the object arm, scattered and reflected by the measured sample, and then returned again to the object lens 58 and beam splitter 57.

On the other hand, the reference light passes the objective lens 60 in the reference arm, is reflected by the reference mirror 61, and then goes through the object lens 60 again to be returned to the beam splitter 57. After returning to the beam splitter 57, the object light and reference light together enter the focusing lens 56 and are then focused onto the optical detector 55 (a photodiode, etc.).

As for the light source of OCT, light having low temporal coherence is used (this is because these lights, when emitted from the same light source at different timings, are highly unlikely to interfere with each other). With Michelson's interferometer that uses light having low temporal coherence as a light source, interference signals manifest only when the distance of the reference arm and object arm is roughly equivalent. As a result, interference signals can be obtained as a function of differential optical path length (interferogram), by measuring the intensity of interference signals using an optical detector while changing the differential optical path length ($\tau$) between the reference arm and object arm.

The shape of this interferogram represents the reflection coefficient distribution of the measured sample 59 in the depth direction, and the structure of the measured sample 59 in the depth direction can be obtained through a one-dimensional scan in the axial direction. In other words, OCT makes it possible to measure the structure of the measured sample 59 in the depth direction by scanning the optical path length.

In addition to scanning in the axial direction as mentioned above, a two-dimensional scan where mechanical scanning is also performed in the lateral direction provides a two-dimensional cross-section image of the measured sample 59. Various scanning apparatuses are available to perform this lateral-direction scan, such as apparatus having a structure whereby the measured sample is moved directly, a structure whereby the object is fixed and only the object lens is shifted, and a structure whereby both the measured object and object lens are fixed and the angle of the galvano mirror placed near the pupil surface of the object lens is turned.

In addition to the aforementioned OCT technology, another technology is known whereby the wavelength spectrum of light reflected by the measured object is acquired by a spectrometer and then the obtained spectral intensity distribution is converted by Fourier transformation. This technology is called "Spectrum interference Optical Coherence Tomography (also known as Fourier Domain OCT, or FD-OCT)" (refer to Patent Literature 2).

Normally with Fourier domain OCT, actual signals that have been acquired (interference signals indicating spectrum interference fringes) are converted by Fourier transformation to retrieve signals in the actual space (OCT signal space). However, acquired spectrum interference fringes are normally actual signals that have no complex information. For this reason, converting these interference fringes by Fourier transformation to acquire OCT signals will result in complex conjugated signals flipped over the axis, as well as auto-correlation signals, manifesting in a manner overlaying with the true OCT signals. These two signals are called "coherent noise" and have negative impact on OCT measurement if overlaid with the true OCT signals. To prevent this from occurring, the range of the measured object must be limited, and the measurement range is limited to a half or even less as a result.

One known traditional method to solve this problem is the phase shift method. Under the phase shift method, multiple spectrum interference fringes relating to the same measured location are acquired while the optical path length of reference light is changed, and phase information (that is, complex information) of the spectrum is restructured from the obtained spectrum interference fringes, in order to erase complex conjugated images.

FIG. 9 is a temporal diagram under the phase shift method. It shows the operation, per one scan cycle, of the galvano mirror used for lateral-direction scanning against time t. (i) shows the operating status trigger of the CCD camera. Here, the CCD camera starts acquiring images at time $t_0$. (ii) indicates the scan position (position in the lateral direction) that changes in discontinuous steps during one scan cycle of the galvano mirror. (iii) indicates the position of the reference mirror moved by means of a piezo element, where measurement is performed multiple times (or three times in this diagram) at each scan step position of the galvano mirror.

Patent Literature 1: Japanese Patent Laid-open No. 2002-310897

Patent Literature 2: Japanese Patent Laid-open No. Hei 11-325849

SUMMARY OF THE INVENTION

Problems to be Solved by the Invention

As evident from the temporal diagram shown in FIG. 9, the conventional phase shift method requires multiple measurements (at least three times) based on different reference optical path lengths at each scan step position of the galvano mirror, i.e., at the same measurement position. This makes the measurement time longer.

Also under the conventional polarization measurement method, it takes a long time to acquire multiple OCT images needed for polarization measurement. Another problem of this method is that to measure multiple measurement ranges, the reference arm position (optical path length) must be changed to acquire multiple images.

The object of the present invention is to solve the aforementioned problems inherent in the conventional methods, and specifically to achieve multiplexing spectrum interference optical coherence tomography capable of achieving full-range OCT measurement that causes no delays in measurement time due to high-order scans and is also free from complex conjugated images or auto-correlation images, by also using time division, polarization division, etc. (here, "multiplexed" means use of time division multiplexing, polarization division multiplexing, multiplexing modulation, etc., in conjunction).

Means for Solving the Problems

To solve the aforementioned problems, the present invention provides spectrum interference optical coherence tomography characterized by comprising: a first beam splitter positioned in the optical path from a light source and used to separate object light and reference light; a scanning apparatus positioned in the optical path of the aforementioned object light and used to scan the aforementioned object light onto a measured object; a second beam splitter positioned in the optical path of the aforementioned reference light; a first reference mirror positioned in the optical path of a first reference light separated by the aforementioned second beam splitter; a second reference mirror positioned in the optical path of a second reference light separated by the aforementioned second beam splitter; and a chopper that passes the aforementioned first reference light and second reference light alternately.

To solve the aforementioned problems, the present invention provides spectrum interference optical coherence tomography characterized by comprising: a beam splitter positioned in the optical path from a light source and used to separate object light and reference light; a scanning apparatus positioned in the optical path of the aforementioned object light and used to scan the aforementioned object light onto a measured object; and a reference mirror positioned in the optical path of the aforementioned reference light and caused to move along the aforementioned optical path to apply continuous phase modulation to the interference signals of the aforementioned object light and reference light.

To solve the aforementioned problems, the present invention provides spectrum interference optical coherence tomography characterized by comprising: a first beam splitter positioned in the optical path from a light source and used to separate object light and reference light; a scanning apparatus positioned in the optical path of the aforementioned object light and used to scan the aforementioned object light onto a measured object; a second beam splitter positioned in the optical path of the aforementioned reference light; a first reference mirror positioned in the optical path of a first reference light separated by the aforementioned second beam splitter and movable along the aforementioned optical path; and a second reference mirror positioned in the optical path of a second reference light separated by the aforementioned second beam splitter and movable along the aforementioned optical path; wherein the aforementioned second reference mirror moves faster than or at a different speed to the aforementioned first reference mirror.

To solve the aforementioned problems, the present invention provides spectrum interference optical coherence tomography characterized by comprising: a beam splitter positioned in the optical path from a light source and used to separate object light and reference light; a scanning apparatus positioned in the optical path of the aforementioned object light and used to scan the aforementioned object light onto a measured object; a spectrometer that receives the aforementioned object light and reference light emitted in a manner overlaying with each other from the aforementioned beam splitter; a first polarization beam splitter positioned in the optical path of the aforementioned reference light; a first reference mirror positioned in the optical path of a first reference light separated by the aforementioned first polarization beam splitter and movable along the aforementioned optical path; a second reference mirror positioned in the optical path of a second reference light separated by the aforementioned first polarization beam splitter and movable along the aforementioned optical path; and a second polarization beam splitter provided in the optical path on the emission side of the aforementioned beam splitter where the light travels toward the spectrometer; wherein the aforementioned second reference mirror moves faster than or at a different speed to the aforementioned first reference mirror.

To solve the aforementioned problems, the present invention provides spectrum interference optical coherence tomography characterized by comprising: a beam splitter positioned in the optical path from a light source and used to separate object light and reference light; a scanning apparatus positioned in the optical path of the aforementioned object light and used to scan the aforementioned object light onto a measured object; a spectrometer that receives the aforementioned object light and reference light emitted in a manner overlaying with each other from the aforementioned beam splitter; a first polarization selector provided in the optical path between the aforementioned light source and beam splitter; and a second polarization selector provided in the optical path on the emission side of the aforementioned beam splitter where the light travels toward the spectrometer; wherein the aforementioned first polarization selector separates the light from the aforementioned light source into a first input light and a second input light that are polarized by 90° with respect to each other, and also passes the first input light and second input light alternately, while the aforementioned second polarization selector separates the light from the aforementioned light source into a first output light and a second output light that are polarized by 90° with respect to each other, and also passes the first output light and second output light alternately.

Spectrum interference optical coherence tomography according to an embodiment of the present invention is characterized in that: the aforementioned first polarization selector comprises a first polarization beam splitter and a second polarization beam splitter both positioned in the optical path from the light source, a reflection mirror that reflects the second input light separated by the aforementioned first polarization beam splitter and causes the light to enter the aforementioned second polarization beam splitter, and a first chopper that passes the aforementioned first input light and second input light alternately; and the aforementioned second polarization selector comprises a third polarization beam splitter and a fourth polarization beam splitter both positioned in the optical path from the light source, a reflection mirror that reflects the second output light separated by the aforementioned third polarization beam splitter and causes the light to enter the fourth polarization beam splitter, and a second chopper that passes the aforementioned first output light and second output light alternately.

To solve the aforementioned problems, the present invention provides spectrum interference optical coherence tomography characterized by comprising: a beam splitter positioned in the optical path from a light source and used to separate object light and reference light; a scanning apparatus positioned in the optical path of the aforementioned object light and used to scan the aforementioned object light onto a measured object; a polarization beam splitter positioned in the optical path of the aforementioned reference light; a spectrometer that receives the aforementioned object light and reference light emitted in a manner overlaying with each other from the aforementioned beam splitter; a polarization selector provided in the optical path between the aforementioned light source and beam splitter; a first reference mirror positioned in the optical path of a first reference light separated by the aforementioned polarization beam splitter and movable along the aforementioned optical path; and a second reference mirror positioned in the optical path of a second reference light separated by the polarization beam splitter and movable along the aforementioned optical path; wherein the aforementioned polarization selector separates the light from the light source into a first input light and a second input light that are polarized by 90° with respect to each other, and also passes the first input light and second input light alternately, and the aforementioned second reference mirror moves faster than or at a different speed to the aforementioned first reference mirror.

EFFECTS OF THE INVENTION

The multiplexing spectrum interference optical coherence tomography pertaining to the present invention is capable of achieving full-range OCT polarization measurement that causes no delays in measurement time due to high-order scans and is also free from complex conjugated images or auto-correlation images, by also using time division, polarization division, etc.

BRIEF DESCRIPTION OF THE DRAWINGS

FIG. 1 Drawing explaining Example 1 pertaining to the present invention.
FIG. 2 Drawing explaining Example 2 pertaining to the present invention.
FIG. 3 Drawing explaining Example 2 pertaining to the present invention.
FIG. 4 Drawing explaining Example 3 pertaining to the present invention.
FIG. 5 Drawing explaining Example 4 pertaining to the present invention.
FIG. 6 Drawing explaining Example 5 pertaining to the present invention.
FIG. 7 Drawing explaining Example 6 pertaining to the present invention.
FIG. 8 Drawing explaining a conventional example.
FIG. 9 Drawing explaining a temporal diagram pertaining to the conventional example.

DESCRIPTION OF THE SYMBOLS 1, 55 Light source
2 Optical path from the light source
3 First beam splitter
4 Object light
5 Reference light
6 Galvano mirror
7, 58, 60 Object lens
8 Measured object
9 Spectrometer
10 Second beam splitter
11, 17 First reference light
12, 18 First reference mirror
13, 20 Second reference light
14 Reflection mirror
15, 21 Second reference mirror
16 Chopper
19 First reference arm
22 Second reference arm
23, 24, 25 CCD image
27 First polarization beam splitter
27' Polarization beam splitter
28, 29 ¼ wave plate
30 Second polarization beam splitter
31 First spectrometer
32 Second spectrometer
32' Spectrometer
33 ¼ wave plate
34 Reflection mirror
35, 61 Reference mirror
36 Reference arm
37 First polarization selector
38 Second polarization selector
39 Optical path of light emitted from the beam splitter
40 First polarization beam splitter
41 Second polarization beam splitter
42 First reflection mirror
43 Second reflection mirror
44 First chopper
45 Third polarization beam splitter
46 Fourth polarization beam splitter
47 Third reflection mirror
48 Fourth reflection mirror
49 Second chopper
50 ½ wave plate
51 Polarizing plate
52 Polarization selector
53 ¼ wave plate
54 Polarization beam splitter
56 Collimator lens
57 Beam splitter
59 Measured sample
62 Focusing lens
63 Optical detector
PZT1 Piezo element
PZT2 Piezo element

BEST MODE FOR CARRYING OUT THE INVENTION

The best mode for carrying out the spectrum interference optical coherence tomography pertaining to the present invention is explained below using examples by referring to the drawings.

Example 1

FIG. 1 (a) is a drawing that explains the overall configuration of Example 1 pertaining to the present invention. In Example 1, lateral-direction scanning is performed using the galvano mirror (one example of lateral-direction scanning apparatus), while the reference mirror is caused to move along the optical path of reference light, along with the use of two reference arms each having a different optical path length, in order to expand the measurement range. To be specific, in Example 1 two OCT images can be obtained simultaneously, each representing a different measurement range.

In other words, Example 1 provides a configuration whereby reference light is alternated between two differential optical path lengths at given scan positions in the lateral direction. Spectral measurement (measurement of spectrum interference fringes) is performed at the respective differential optical path lengths, after which the lateral-direction position is moved and then spectrum interference fringes are measured there in a similar manner.

In FIG. 1 (a), a first beam splitter 3 is positioned in an optical path 2 from a light source 1. The first beam splitter 3 separates the received light into an object light 4 traveling along an extended line of the optical path 2, and a reference light 5 traveling in the orthogonal direction crossing with the optical path at 90°. A galvano mirror 6 is positioned in the optical path on which the object light from the first beam splitter 3 travels.

An object lens 7 is positioned in the optical path of the object light reflected by the galvano mirror 6, and the object light is focused onto a measured object. The object light focused onto and reflected by a measured object 8 returns to the first beam splitter 3, is reflected sideways in a manner overlaying with the reference light, and then enters a spectrometer 9 having a CCD camera for receiving this light.

Although its details are not explained, the spectrometer 9 is configured in such a way that it can convert into digital data the object light and reference light received by the CCD camera and can convert the obtained data by Fourier transformation on a PC.

A second beam splitter 10 is provided in the optical path of the reference light separated by the first beam splitter 3. A first reference mirror 12 is positioned in the optical path of a first reference light 11 reflected in the right-angle direction by the second beam splitter 10. A reflection mirror 14 is positioned in the optical path of a second reference light 13 passing through the second beam splitter 10, where this reflection mirror reflects the second reference light 13 in the right-angle direction. A second reference mirror 15 is positioned in the optical path of the second reference light 13 reflected by this reflection mirror 14 in the right-angle direction.

Although the optical path of the first reference light 11 is parallel with the optical path of the second reference light 13, a chopper 16 (rotary shutter) is provided in a manner alternately cutting off these optical paths of the first reference light 11 and second reference light 13.

Based on this configuration, separation of reference light by the beam splitter generates two types of reference light having different path lengths, one along the optical path of the first reference light 11 and the other along the optical path of the second reference light 13, and these reference lights are returned alternately, by means of the chopper 16, into the second beam splitter 10 and then to the first beam splitter 3, after which the returned reference lights are overlaid with the object light to enter the spectrometer 9.

FIG. 1 (b) is a drawing that provides a temporal diagram pertaining to Example 1. It shows the operation, per one scan cycle ($t_0$ to $t_n$), of the galvano mirror 6 against time t. (i) is a diagram showing the operating status (ON or OFF) of the CCD camera. The CCD camera starts acquiring images at time $t_0$.

(ii) indicates the control status of the galvano mirror 6, where the vertical axis represents the scan position (position in the lateral direction) that changes in discontinuous steps over a fixed time interval T (one scale in the diagram) during one scan cycle of the galvano mirror 6. (iii) indicates the position of the reference mirror 15 that changes alternately by means of the chopper 16.

According to Example 1, the position of the reference mirror 15 varies and the first reference light 11 and second reference light 13, each having a different path length, are overlaid with the object light at alternate timings to enter the spectrometer 9. As a result, two different measurement ranges can be measured at alternate timings.

Example 2

FIG. 2 (a) is a drawing that explains the overall configuration of Example 2 pertaining to the present invention. As in Example 1, in Example 2 lateral-direction scanning is also performed using the galvano mirror (one example of lateral-direction scanning apparatus), while the reference mirror is caused to move along the optical path of reference light, in order to achieve phase shift by means of changing the optical path length of reference light.

Unlike in Example 1, however, this configuration is designed to change the optical path length of each of the two reference lights in discontinuous steps during one scan cycle of the galvano mirror 6, thereby changing the phase shift and measuring spectrum interference fringes.

In FIG. 2 (a), the first beam splitter 3 is positioned in the optical path 2 from the light source 1. The first beam splitter 3 separates the received light into the object light 4 traveling along an extended line of the optical path 2, and the reference light 5 traveling in the orthogonal direction crossing with the optical path 2 at 90°. The galvano mirror 6 is positioned in the optical path on which the object light from the first beam splitter 3 travels.

The object lens 7 is positioned in the optical path of the object light reflected by the galvano mirror 6, and the object light is focused onto the measured object 8. The object light focused onto and reflected by the measured object 8 returns to the first beam splitter 3 again, is reflected sideways in a manner overlaying with the reference light, and then enters the spectrometer 9.

The second beam splitter 10 is provided in the optical path of the reference light 5 separated by the first beam splitter 3. A first reference mirror 18 is positioned in the optical path of a first reference light 17 passing through the second beam splitter 10, and constitutes a first reference arm 19. A second reference mirror 21 is positioned in the optical path of a second reference light 20 reflected in the right-angle direction by the second beam splitter 10, and constitutes a second reference arm 22.

One key characteristics of the configuration presented by Example 2 is that it allows the first reference mirror 18 and second reference mirror 21 to move along the respective optical paths by means of piezo elements PZT1, PZT2, respectively. This configuration causes the first reference light 17 and second reference light 20 to change their respective path lengths, thereby generating the first reference light 17 and second reference light 20, each undergoing a different phase modulation.

The moving distances of the first reference mirror 18 and second reference mirror 21 must be longer than the coherent length, or specifically they must be several times longer than the coherent length. This way, the first reference light 17 and second reference light 20 will be overlaid with the object light, without interfering with each other, to demonstrate the function required of reference light.

FIG. 2 (b) is a drawing that provides a temporal diagram pertaining to Example 2. It shows the operation, per one scan cycle, of the galvano mirror 6 against time t. (i) indicates the status of the operation trigger signal of the CCD camera. Here, the CCD camera starts acquiring images at time $t_0$. (ii) indicates the scan position (position in the lateral direction) that changes in discontinuous steps during one scan cycle of the galvano mirror 6.

(iii) is a diagram showing the position of the first reference mirror 18 on the first reference arm 19, where the position is changed by means of the piezo element PZT1. The first reference mirror 18 moves across its entire movable range (wavelength) in discontinuous steps over the time interval T during one scan cycle of the galvano mirror 6.

(iv) is a diagram showing the position of the second reference mirror 21 on the second reference arm 22, where the position is changed by means of the piezo element PZT2. The second reference mirror 21 moves across its entire movable range (wavelength) twice in discontinuous steps over the time interval T/2 during one scan cycle of the galvano mirror 6.

FIGS. 3 (a) through (c) show the images of fringe patterns acquired by the CCD camera in accordance with Example 2. In these figures, the horizontal axis represents the CCD pixel (position on the CCD image in the lateral direction), while the vertical axis represents the measurement number (number of measurements). An image 23 of FIG. 3 (a) shows a fringe pattern image corresponding to (iii) in FIG. 2 (b), while an image 24 of FIG. 3 (b) shows a fringe pattern image corresponding to (iv) in FIG. 2 (b). FIG. 3 (c) indicates a fringe pattern image 25 obtained by overlaying the image 23 of FIG. 3 (a) and the image 24 of FIG. 3 (b).

As evident from these images 23, 24, the image 24 has a greater angle of inclination from the vertical direction compared to the image 23. FIGS. 3 (d) and (e) show spectral intensity distributions at X-X positions corresponding to the two images 23, 24, respectively. From these figures, clearly the spatial frequency of the spectral intensity distribution based on the fringe pattern in the image 24 is denser compared to the spatial frequency pertaining to the image 23.

Although a spectral intensity distribution at X-X positions is not provided with respect to the image 25, it should correspond to a distribution obtained by overlaying two spectral intensity distributions having different spatial frequencies, one sparse and one dense, as shown in FIGS. 3 (d) and (e). FIGS. 3 (f) and (g) represent the Fourier transformed versions of the images shown by FIGS. 3 (d) and (e).

As explained above, Example 2 allows for measurement of the fringe patterns shown in the images 23 and 24, respectively, by properly separating the respective characteristics and without having to alternate lights at different timings using a chopper, etc., as shown in the image 25 of FIG. 3 (c). Consequently, two OCT images can be obtained in one measurement.

Example 3

FIG. 4 is a drawing that explains Example 3 pertaining to the present invention. Example 3 is the same as Example 2, except that the first reference light 17 by the first reference arm 19 is vertically polarized, while the second reference light 20 by the second reference arm 22 is horizontally polarized, in a manner preventing the two reference lights from interfering with each other.

In FIG. 4, the beam splitter 3 is positioned in the optical path 2 from the light source 1. The beam splitter 3 separates the received light into the object light 4 traveling along an extended line of the optical path 2 from the light source 1, and the reference light 5 traveling in the orthogonal direction crossing with the optical path at 90°. The galvano mirror 6 is positioned in the optical path on which the object light from the beam splitter 3 travels.

A first polarization beam splitter 27 is provided in the optical path of the reference light separated by the first beam splitter 3. The first reference mirror 18 is positioned in the optical path of the first reference light 17 passing through the first polarization beam splitter 27, and constitutes the first reference arm 19. The second reference mirror 21 is positioned in the optical path of the second reference light 20 reflected in the right-angle direction by the first polarization beam splitter 27, and constitutes the second reference arm 22.

The reference mirror 1 and reference mirror 2 are fixed in a manner not moving along their respective optical paths. Then, the ¼ wave plates 28, 29 are positioned on the first reference arm and the second reference arm, respectively. Based on this configuration, the first reference light 17 and second reference light 20, whose polarization directions are different from each other by 90°, are generated.

The object lens 7 is positioned in the optical path of the object light reflected by the galvano mirror 6, and the object light is focused onto the measured object 8. A second polarization beam splitter 30 is positioned on the emission side of the galvano mirror 6 where the light travels toward the spectrometer 9. The object light focused onto and reflected by the measured object 8 returns to the first beam splitter 3 again, and is then emitted toward the second beam splitter 10 together with the reference light.

If light polarized by 45° enters the beam splitter from the light source 1, the aforementioned configuration allows, by means of the first reference arm and the second reference arm and also through the first polarization beam splitter 27, for splitting of the reference light 5, having been reflected in the cross-angle direction, into two lights, or specifically the first reference light 17 and second reference light 20, both polarized to provide a 90° difference in between.

The two reference lights 17, 20 are simultaneously overlaid with the object light 4 and enter the second polarization beam splitter 30 from the beam splitter 3. The first reference light 17 that has been polarized vertically, and a part of the object light, enter a first spectrometer 31 after passing the second polarization beam splitter. On the other hand, the second reference light 20 that has been polarized horizontally, and a part of the object light, enter a second spectrometer 32 after reflecting in the right-angle direction at the second polarization beam splitter 30. This way, the images acquired by the first and second spectrometers 31, 32 can be converted by Fourier transformation to simultaneously obtain multi-range spectrum interference images.

Example 4

FIG. 5 is a drawing that explains Example 4 pertaining to the present invention. Example 4 is the same as Example 2, except that the first reference light 17 by the first reference arm 19 is vertically polarized, while the second reference light 22 by the second reference arm is horizontally polarized, in a manner preventing the two reference lights from interfering with each other.

In FIG. 5, the beam splitter 3 is positioned in the optical path 2 from the light source 1. The beam splitter 3 separates the received light into the object light 4 traveling along an extended line of the optical path 2 from the light source 1, and the reference light 5 traveling in the orthogonal direction crossing with the optical path at 90°. The galvano mirror 6 is positioned in the optical path on which the object light from the beam splitter 3 travels.

A polarization beam splitter 27' is provided in the optical path of the reference light separated by the beam splitter 3. The first reference mirror 18 is positioned in the optical path of the first reference light 17 passing through the polarization beam splitter 27', and constitutes the first reference arm 19. The second reference mirror 21 is positioned in the optical path of the second reference light 20 reflected in the right-angle direction by the polarization beam splitter 27', and constitutes the second reference arm 22.

The first reference mirror 18 and second reference mirror 21 are movable along their respective optical paths via the piezo elements PZT1, PZT2. Then, the ¼ wave plates 28, 29 are positioned on the first reference arm and the second reference arm, respectively. Based on this configuration, the first reference light 17 and second reference light 20, whose polarization directions are different from each other by 90° and whose path length can be changed, respectively, are generated.

The object lens 7 is positioned in the optical path of the object light reflected by the galvano mirror 6, and the object light is focused onto the measured object 8. The second polarization beam splitter 30 is positioned on the emission side of the galvano mirror 6 where light travels toward the spectrometer 9. The object light focused onto and reflected by the measured object 8 returns to the first beam splitter 3 again, and is then emitted toward the second beam splitter 10 together with the reference light.

If light polarized by 45° enters the beam splitter from the light source 1, the aforementioned configuration allows, by means of the first reference arm and the second reference arm and also through the polarization beam splitter 27', for splitting of the reference light 5, having been reflected in the cross-angle direction, into two lights, or specifically the first reference light 17 and second reference light 20, both polarized to provide a 90° difference in between and each having a different optical path length.

The first reference light 17 that has been polarized vertically, and the second reference light 20 that has been polarized horizontally, are simultaneously overlaid with the object light 4 and enter a spectrometer 32' from the beam splitter 3. This way, the images acquired by the spectrometers 32' can be converted by Fourier transformation to simultaneously obtain multi-range spectrum interference images.

Example 5

FIG. 6 is a drawing that explains Example 5 pertaining to the present invention. In FIG. 6 (a), the beam splitter 3 is positioned in the optical path 2 from the light source 1. The beam splitter 3 separates the received light into the object light 4 traveling along an extended line of the optical path, and the reference light 5 traveling in the orthogonal direction crossing with the optical path at 90°. The galvano mirror 6 is positioned in the optical path on which the object light from the beam splitter 3 travels.

The object lens 7 is positioned in the optical path of the object light reflected by the galvano mirror 6, and the object light is focused onto the measured object 8. The object light focused onto and reflected by the measured object 8 returns to the beam splitter 3 again, and is then emitted sideways and enters the spectrometer 9 together with the reference light.

A ¼ wave plate 33 and a reflection mirror 34 are positioned in the optical path of the reference light separated by the beam splitter 3, while a reference mirror 35 is positioned in the optical path of the reference light 5 reflected in the right-angle direction by the first reflection mirror 34 and a reference arm 36 is thus formed.

Based on this configuration, the reference light 5 separated by the beam splitter 3 is reflected and then polarized by +45° or −45° by means of the ¼ wave plate 33, reflection mirror 34 and reference mirror 35, and finally returns to the beam splitter 3, after which the returned reference light is overlaid with the object light and emitted toward the spectrometer 9.

As explained above, the configuration presented by Example 5 is characterized by the positioning of a first polarization selector 37 on the optical path 2 side (input light path of the interferometer) of light entering the beam splitter 3 from the light source 1, along with the positioning of a second polarization selector 38 on an optical path 39 side (output light path of the interferometer) of light emitted by the beam splitter 3.

The first polarization selector 37 has a first polarization beam splitter 40 and a second polarization beam splitter 41 positioned in the optical path 2, and a first light H passing through these polarization beam splitters 40, 41 and thus polarized horizontally is caused to enter the beam splitter 3.

Also provided is a first reflection mirror 42 that reflects a second light V, which has been polarized vertically by the first polarization beam splitter 40 and thus aimed in the right-angle direction. Furthermore, a second reflection mirror 43 is provided that reflects toward the second polarization beam splitter 41 the second light V reflected by the first reflection mirror 42.

The optical path connecting the first polarization beam splitter 40 to the second polarization beam splitter 41, and the optical path connecting the first reflection mirror 42 to the second reflection mirror 43, are parallel with each other, and a first chopper 44 (rotary shutter) is provided to cut off these two optically paths at alternate timings. This first chopper 44 causes the first light H and second light V, polarized by 90° in the horizontal and vertical directions, respectively, to be selectively passed at specified alternate timings to enter the beam splitter 3.

The second polarization selector 38 has a third polarization beam splitter 45 and a fourth polarization beam splitter 46 positioned in the optical path 39, and of the object light and reference light emitted by the beam splitter 3 the horizontally polarized light passes through the third polarization beam splitter 45 and fourth polarization beam splitter 46 and is emitted toward the spectrometer 9.

Also provided is a third reflection mirror 47 that reflects the light that has been polarized vertically by the third polarization beam splitter 45 and thus aimed in the right-angle direction. Furthermore, a fourth reflection mirror 48 is provided that reflects toward the fourth polarization beam splitter 46 the light reflected by the second reflection mirror 43.

The optical path connecting the third polarization beam splitter 45 to the fourth polarization beam splitter 46, and the optical path connecting the second reflection mirror 43 to the fourth reflection mirror, are parallel with each other, and a second chopper 49 (rotary shutter) is provided to alternately cut off these two optical paths timewisely.

In addition, the emission side of the fourth polarization beam splitter 46 has a ½ wave plate 50. The first output light H and second output light V, polarized in the horizontal and vertical directions, respectively, by the second chopper 49, are passed at alternate timings, travel through the fourth polarization beam splitter 46 and ½ wave plate 50, and are emitted toward the spectrometer 9 from the second polarization selector 38.

A polarizing plate 51 is provided on the emissions side of the second polarization selector 38, to cause the light emitted from the second polarization selector 38 to be always polarized in the same direction toward the spectrometer 9.

The operation of Example 5 is explained below. The light from the light source 1 is polarized into the horizontally polarized light H and vertically polarized light V at alternate timings at the first polarization selector 37, and each polarized light enters the beam splitter 3. The object light 4 separated by the beam splitter 3 is scanned and irradiated onto the measured object 8 via the galvano mirror 6, and the reflected light returns to the beam splitter 3.

The reference light 5 separated by the beam splitter 3 travels through the reference arm 36 comprising the ¼ wave plate 33, reflection mirror 34 and reference mirror 35, and finally returns to the beam splitter 3. The object light and reference light thus returned to the beam splitter 3 are both selected by the second polarization selector 38 at alternate timings as horizontally polarized output light H and vertically polarized output light V, to be passed through the ½ wave plate 50 and polarizing plate 51 for final entry into the spectrometer.

FIG. 6 (b) is a temporal diagram showing the operation, per one scan cycle of the galvano mirror 6 shown in Example 5. (i) is a diagram showing the imaging ready status of the CCD camera. As shown, the CCD camera starts acquiring images at time $t_0$. (ii) indicates the scan position (position in the lateral direction) that changes in discontinuous steps during one scan cycle of the galvano mirror 6.

(iii) shows the first light H polarized horizontally, and the second light V polarized horizontally, both of which are passed selectively at alternate timings by means of the first chopper 44 at the first polarization selector 37. (iv) shows the first output light H polarized horizontally, and the second output light V polarized horizontally, both of which are passed selectively at alternate timings by means of the second chopper 49 at the second polarization selector 38.

As revealed by (iii) and (iv) of this temporal diagram, four measurements based on the combinations HV, HH, VH and VV of the horizontally polarized light H and vertically polarized light V, respectively selected by the first polarization selector 37 and second polarization selector 38, can be obtained during each time interval T. As a result, polarization OCT measurement can be achieved at very high speed. By multiplexing polarization measurements via time division as explained above, high-speed polarization OCT measurement becomes possible, which is very effective in an OCT measurement application where double refraction information of samples must be measured.

Example 6

FIG. 7 is a drawing that explains Example 6 pertaining to the present invention. As shown in FIG. 7 (a), this example is the same as Example 5, except that the second polarization selector 38 on the emission side is removed. In place of the removed polarization selector, two reference arms similar to those shown in FIG. 4 of Example 3 are provided, each handling a reference light polarized in a different direction using a polarization beam splitter, in order to perform simultaneous measurements using two reference lights and one spectrometer (single detector) 9.

Also, the scan speeds of the two reference-light reference mirrors (here, "scan" refers to movement along the optical path of each reference mirror, and is also called "M-Scan") are set differently, and this results in a different modulation frequency (spatial frequency) of the spectral intensity distribution along each axis of interference fringes. Consequently, the window function position for the signal spectrum can be shifted during phase restructuring via Fourier transformation, thereby allowing the respective signals to be separated.

The specific apparatus used in Example 6 has, as shown in FIG. 7 (a), a polarization selector 52, a ¼ wave plate 53 and the beam splitter 3 positioned in the optical path 2 from the light source 1. The beam splitter 3 separates the received light into the object light 4 traveling along an extended line of the optical path 2, and the reference light 5 traveling in the orthogonal direction crossing with the optical path at 90°. The galvano mirror 6 is positioned in the optical path on which the object light from the beam splitter travels.

The object lens 7 is positioned in the optical path of the object light reflected by the galvano mirror 6, and the object light is focused onto the measured object 8. The object light focused onto and reflected by the measured object 8 returns to the beam splitter again, and is then reflected sideways and enters the spectrometer 9 together with the reference light.

A polarization beam splitter 54 is positioned in the optical path of the reference light 5 separated from the beam splitter 3. In the optical path of the first reference light 17 passing the polarization beam splitter 54, the ¼ wave plate 28 and first reference mirror 18 are positioned to constitute the first reference arm 19. The first reference mirror 18 can be moved along the optical path by means of the piezo element PZT1, to allow for adjustment of the path length. The ¼ wave plate 28 of the first reference arm 19 causes the first reference light 17, which has been polarized vertically, to be returned to the beam splitter 3 again.

In the optical path of the second reference light reflected in the right-angle direction by the polarization beam splitter 54, the ¼ wave plate 29 and second reference mirror 21 are positioned to constitute the second reference arm 22. The second reference mirror 21 can be moved along the optical path by means of the piezo element PZT2, to allow for adjustment of the path length. The ¼ wave plate 29 of the second reference arm 22 causes the second reference light 20, which has been polarized horizontally, to be returned to the beam splitter 3 again.

The polarization selector 52 has a configuration similar to the one explained in connection with Example 5. The first polarization beam splitter 40 and second polarization beam splitter 41 are positioned in the optical path 2, and the first light, passing these first polarization beam splitter 40 and second polarization beam splitter 41 and thus polarized horizontally, is emitted toward the beam splitter.

Also provided is the first reflection mirror 42 that reflects the second light, which has been polarized vertically by the first polarization beam splitter 40 and thus aimed in the right-angle direction. Furthermore, the second reflection mirror 43 is provided that reflects toward the second polarization beam splitter 41 the second light reflected by the first reflection mirror 42. This way, the second light polarized horizontally by the first polarization beam splitter 40 is emitted toward the beam splitter 3.

The optical path connecting the first polarization beam splitter 40 to the second polarization beam splitter 41, and the optical path connecting the first reflection mirror 42 to the second reflection mirror 43, are parallel with each other, and the first chopper 44 (rotary shutter) is provided to cut off these first optical path and second optical path.

This first chopper 44 causes the first light H and second light V, polarized in the horizontal and vertical directions, respectively, to be passed at specified alternate timings and emitted from the second polarization beam splitter 41. The emitted first light is polarized by +45°, while the emitted second light is polarized by −45°, both in the vertical direction, by means of the ¼ wave plate 53, for entry into the beam splitter 3.

According to Example 6, the polarization selector 52 causes lights having different path lengths and polarization conditions to enter the beam splitter 3 at alternative timings and also to separate into the object light 4 and the reference light 5. The reference light 5, in the form of either the polarized reference light 17 or 20, returns to the beam splitter 3 with its path length adjusted, and then enters the spectrometer 9 together with the object light 4. As a result, alternate measurements become possible using two lights, each having a different measurement range and polarized with respective to the other light and whose path length has been adjusted.

FIG. 7 (b) is a temporal diagram showing the operation of each equipment, etc., per one scan cycle, of the galvano mirror 6 shown in Example 6. Here, (i) through (iii) are the same as the corresponding diagrams in FIG. 6 (b). Specifically, (i) is a diagram showing the imaging ready status of the CCD camera of the spectrometer 9 (the CCD camera starts acquiring images at $t_0$). (ii) is a diagram showing the control status of the galvano mirror 6. (iii) is a diagram showing alternate selections of the first light H and second light V, polarized in the horizontal and vertical directions, respectively, by the polarization selector 52.

(iv) is a diagram showing the position of the first reference mirror 18 on the first reference arm 17, where the position is changed by means of the piezo element PZT1. The first reference mirror 18 moves across its entire movable range (wavelength) in discontinuous steps over the time interval T during one scan cycle of the galvano mirror 6.

(v) is a diagram showing the position of the second reference mirror 21 on the second reference arm 22, where the position is changed by means of the piezo element PZT2. The second reference mirror 21 moves across its entire movable range (wavelength) twice in discontinuous steps over the time interval T/2 during one scan cycle of the galvano mirror 6. Here, the position change of the second reference mirror 21 on the second reference arm 22 by means of the piezo element PZT2 need not follow the pattern shown in (v), and a modulation similar to (v) can also be simulated based on a position change pattern resembling a sine wave or cosine wave.

In Example 6, the first reference mirror 18 on the first arm 17 is moved at twice the speed of the second reference mirror 21 on the second arm 22, as shown above. This way, the spectral intensity distribution of an image that consists of two overlaid images having sparse and dense spatial frequencies, respectively, can be obtained using the spectrometer 9, in the same manner as explained in FIG. 3 of Example 2. By converting the obtained spectral intensity distribution via Fourier transformation, the fringe patterns shown in images 1 and 2 corresponding to FIGS. 3 (f) and (g) can be measured by properly separating their characteristics. Consequently, this allows two OCT images to be obtained in one measurement.

In short, in Example 6 the first light H and second light V, polarized in the horizontal and vertical directions, respectively, by the polarization selector 52, are alternately selected, and two OCT images can be obtained in one measurement for each of these first light H and second light V, by means of the reference light 17 polarized horizontally and the reference light 20 polarized vertically. As a result, a total of four images can be obtained in one measurement, and this makes high-speed measurement possible.

The best mode for carrying out the present invention was explained above using examples. It should be noted, however, that the present invention is not at all limited to these examples, and it can be applied in a number of ways within the scope of technical elements described in the Scope of Claims.

INDUSTRIAL FIELD OF APPLICATION

The present invention adopts the configuration explained above to enable nondestructive tomographic measurement over the full range at high speed. Therefore, the present invention can be applied as a type of nondestructive tomographic measurement technology suitable in ophthalmology and other medical fields as well as for other industrial measurements.

The invention claimed is:

1. An apparatus for spectrum interference optical coherence tomography characterized by comprising:
   a first beam splitter positioned in an optical path from a light source and used to separate object light and reference light;
   a scanning apparatus positioned in an optical path of the object light and used to scan the object light onto a measured object;
   a second beam splitter positioned in an optical path of the reference light;
   a first reference mirror positioned in an optical path of a first reference light separated by the second beam splitter;
   a second reference mirror positioned in an optical path of a second reference light separated by the second beam splitter; and
   a chopper that passes the first reference light and second reference light alternately.

2. An apparatus for spectrum interference optical coherence tomography characterized by comprising:
   a beam splitter positioned in an optical path from a light source and used to separate object light and reference light;
   a scanning apparatus positioned in an optical path of the object light and used to scan the object light onto a measured object;
   a spectrometer that receives the object light and reference light emitted in a manner overlaying with each other from the beam splitter;
   a first polarization beam splitter positioned in an optical path of the reference light;
   a first reference mirror positioned in an optical path of a first reference light separated by the first polarization beam splitter and movable along the optical path;
   a second reference mirror positioned in an optical path of a second reference light separated by the first polarization beam splitter and movable along the optical path; and
   a second polarization beam splitter provided in an optical path on the emission side of the beam splitter where the light travels toward the spectrometer;
   wherein the second reference mirror moves faster or at a different speed than the first reference mirror.

3. An apparatus for spectrum interference optical coherence tomography characterized by comprising:
   a beam splitter positioned in an optical path from a light source and used to separate object light and reference light;
   a scanning apparatus positioned in an optical path of the object light and used to scan the object light onto a measured object;
   a spectrometer that receives the object light and reference light emitted in a manner overlaying with each other from the beam splitter;

a first polarization selector provided in an optical path between the light source and beam splitter; and a second polarization selector provided in an optical path on the emission side of the beam splitter where the light travels toward the spectrometer;

wherein the first polarization selector separates the light from the light source into a first input light and a second input light that are polarized by 90° with respect to each other, and also passes the first input light and second input light alternately; and wherein the second polarization selector separates the light from the light source into a first output light and a second output light that are polarized by 90° with respect to each other, and also passes the first output light and second output light alternately;

wherein the first polarization selector comprises a first polarization beam splitter and a second polarization beam splitter both positioned in the optical path from the light source, a reflection mirror that reflects the second input light separated by the first polarization beam splitter and causes the light to enter the second polarization beam splitter, and a first chopper that passes the first input light and second input light alternately; and wherein the second polarization selector comprises a third polarization beam splitter and a fourth polarization beam splitter both positioned in the optical path from the light source, a reflection mirror that reflects the second output light separated by the third polarization beam splitter and causes the light to enter the fourth polarization beam splitter, and a second chopper that passes the first output light and second output light alternately.

4. An apparatus for interference optical coherence tomography characterized by comprising:

a beam splitter positioned in an optical path from a light source and used to separate object light and reference light;

a scanning apparatus positioned in an optical path of the object light and used to scan the object light onto a measured object;

a polarization beam splitter positioned in an optical path of the reference light;

a spectrometer that receives the object light and reference light emitted in a manner overlaying with each other from the beam splitter;

a polarization selector provided in an optical path between the light source and beam splitter;

a first reference mirror positioned in an optical path of a first reference light separated by the polarization beam splitter and movable along the optical path; and a second reference mirror positioned in an optical path of a second reference light separated by the polarization beam splitter and movable along the optical path;

wherein the polarization selector separates the light from the light source into a first input light and a second input light that are polarized by 90° with respect to each other, and also passes the first input light and second input light alternately; and wherein the second reference mirror moves faster or at a different speed than the first reference mirror.

* * * * *